(12) United States Patent
Ueno et al.

(10) Patent No.: US 6,215,012 B1
(45) Date of Patent: Apr. 10, 2001

(54) PREPARATION OF ORGANOHALOSILANES

(75) Inventors: Susumu Ueno; Toshio Shinohara; Mikio Aramata, all of Annaka; Yoichi Tanifuji, Tokyo; Tetsuya Inukai, Annaka; Kazutoshi Fujioka, Gunma-ken, all of (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/657,458

(22) Filed: Sep. 7, 2000

(30) Foreign Application Priority Data

Jun. 8, 2000 (JP) .................................. 12-171419

(51) Int. Cl.$^7$ ...................................................... C07F 7/16
(52) U.S. Cl. ............................................................. 556/472
(58) Field of Search ............................................... 556/472

(56) References Cited

U.S. PATENT DOCUMENTS

| 4,602,101 | 7/1986 | Halm et al. . |
| 4,762,940 | 8/1988 | Halm et al. . |
| 6,005,130 | * 12/1999 | Lewis et al. .......................... 556/472 |

FOREIGN PATENT DOCUMENTS

| 617569 | 1/1959 | (SU) . |
| 903369 | 6/1964 | (SU) . |
| 1152943 | 11/1969 | (SU) . |

OTHER PUBLICATIONS

English translation of USSR 617,569 (no date).
Frank Komitsky, Jr., et al., "The Influence of Promoter Levels on the Direct Synthesis," *Silicon for the Chemial Industry IV*, Geiranger, Norway, pp. 217–225 (1998).
L. Roesch et al., "The Starting Phase of the MCS–Direct Synthesis, Some Experimental Observations," *Siliconf or the Chemical Industry III*, Sandefjord, Norway, pp. 269–273 (1996).
T.Hayashi et al., "Dichloro[1,1'–bis(diphenylphosphino)ferrocene]palladium–(II): An Effective Catalyst for Cross–Coupling of Secondary and Primary Alkyl Grignard and Alkylzinc Reagents with Organic Halides," *J. Am. Soc.*, 106, pp. 158–163 (1984).

* cited by examiner

Primary Examiner—Paul F. Shaver
(74) Attorney, Agent, or Firm—Millen, White, Zelano & Branigan

(57) ABSTRACT

When oganohalosilanes are prepared by charging a reactor with a contact mass containing a metallic silicon powder and a copper catalyst, and introducing an organohalide-containing gas into the reactor to effect the direct reaction, a metal complex of an organophosphino compound is added to the contact mass. The invention is successful in producing organohalosilanes at a significantly improved production rate without reducing the selectivity of useful silane.

7 Claims, No Drawings

PREPARATION OF ORGANOHALOSILANES

This invention relates to a process for preparing organohalosilanes, and more particularly, to an industrial process for preparing organohalosilanes by direct synthesis while improving the production rate of useful silane.

BACKGROUND OF THE INVENTION

With respect to the synthesis of alkylhalosilanes, Rochow first disclosed in U.S. Pat. No. 2,380,995 direct synthesis reaction between metallic silicon and alkyl halide in the presence of a copper catalyst. Since then, there have been reported a number of research works relating to various co-catalysts used together with copper catalysts, reactors, additives used during reaction, and the like. In the industrial synthesis of organohalosilanes, the selectivity of diorganodihalosilane which is most widely used in silicone resins, the formation rate of silanes, and the percent conversion of metallic silicon into useful silane are crucial. The selectivity of diorganodihalosilane is evaluated in terms of a weight or molar ratio of dialkyldihalosilane to the silanes produced and a T/D ratio. Organohalosilane products contain diorganodihalosilane (D), triorganohalosilane (M), organotrihalosilane (T), etc. as well as other by-products such as organohydrodihalosilane (H) and organohalodisilane. In particular, disilanes are known as a high-boiling fraction among silicone manufacturers because few processes are available for the effective utilization of disilanes, and most disilanes are discarded. The T/D ratio is a compositional ratio of organotrihalosilane to diorganodihalosilane in the entire organohalosilanes produced, with a lower T/D ratio being preferred. The formation rate of diorganohalosilane is represented by a space time yield (STY) which is the weight of crude diorganohalosilane produced per unit time relative to the weight of metallic silicon held in the reactor. In order to improve the content of diorganohalosilane produced, reduce the T/D ratio or increase the STY, various research works have been made with a focus on the catalyst and promoter.

USSR Application Specification No. 617,569 (Certificate of inventorship No. 122,749) dated Jan. 24, 1959 discloses reaction in the presence of metallic silicon-copper alloy with 20 to 40 ppm of antimony added. Allegedly, the dimethyldichlorosilane content is improved from 40% to 60%. U.S. Pat. No. 4,500,724 discloses use of a copper/zinc/tin catalyst containing 200 to 3,000 ppm of tin, thereby achieving an improvement of T/D to 0.037. Japanese Patent Publication (JP-B) No. 6-92421 discloses reaction using copper arsenide having an arsenic concentration of at least 50 ppm. It is described in these patent references that reactivity, more specifically the rate of reaction of metallic silicon is improved by adding these tin, antimony and arsenic co-catalysts to a reaction contact mass comprising metallic silicon and copper.

USSR Application Specification No. 903,369 (Certificate of inventorship No. 178,817) dated Jun. 2, 1964 discloses that a co-catalyst selected from the group consisting of zinc, bismuth, phosphorus (200 ppm), arsenic, tin, and iron improves the dimethyldichlorosilane content to 72.1% from the value achieved by the above-referred Application Specification No. 617,569 (Certificate of inventorship No. 122, 749). Also USSR Application Specification No. 1,152,943 (Certificate of inventorship No. 237,892) dated Nov. 20, 1969 discloses to add a phosphorus-copper-silicon alloy to a contact mass so as to give 2,500 to 30,000 ppm of phosphorus, thereby improving the dimethyldichlorosilane content to 82.3%. Moreover, U.S. Pat. No. 4,602,101 corresponding to JP-B 5-51596 discloses that 25 to 2,500 ppm of a phosphorus compound capable of generating elemental phosphorus in the reactor is added to a contact mass. Although the results of reaction according to this U.S. patent are improved over the last-mentioned USSR patent, there still remain many problems including hazard imposed by spontaneously igniting elemental phosphorus and increased cost of raw materials. Then this U.S. patent is also unsuitable to apply to commercial scale reactors. Also, F. Komitsky et al., Silicon For the Chemical Industry IV, Geiranger, Norway (1998), page 217, proposes the addition of phosphorus in the form of copper phosphide, leaving problems including a low percent conversion, ineffective utilization of phosphorus, and difficult control of a phosphorus concentration. U.S. Pat. No. 6,025,513 discloses to add boron to a contact mass wherein the boron concentration is controlled so as to improve productivity. U.S. Pat. No. 5,059,706 discloses to introduce a phosphorus compound in a vapor phase into a reactor for increasing selectivity. U.S. Pat. No. 6,005,130 discloses to introduce organomonophosphine for increasing selectivity.

However, the phosphorus base additives used in the prior art have an outstanding trade-off between activity and composition selectivity. In particular, it is pointed out that oxide originating from phosphorus can exacerbate flow on the particle surface. Therefore, the conventional phosphorus base additives offer few merits on the continuous operation of commercial scale reactors. Other additives are known from L. Rosch, W. Kalchauer et al., Silicon for the Chemical Industry IV, Sandefjord, Norway (1996) wherein monomethyldichlorosilane is introduced for improving activity. This additive is effectively only at the initial period, but not regarded as exerting a lasting effect during the continuous operation of commercial scale reactors.

A prior art gas phase low-molecular weight compound is difficult to precisely control high-temperature reaction because it has a low evaporation temperature and lacks thermal stability. Additionally, none of these prior art processes can control the distance between atoms having catalysis.

SUMMARY OF THE INVENTION

An object of the invention is to provide a process for preparing organohalosilanes by the direction method while increasing the rate of production of useful silane.

From a different point of view which has never been taken in the prior art, we have found that a complex having an organophosphino compound as a ligand is an activator having a unique function, especially effective for improving the rate of production of useful silane.

Conventional additives which are known effective to improve the useful silane content are phosphorus compounds including metallic phosphorus, phosphorus oxide, copper phosphide, tin phosphide, zinc phosphide, aluminum phosphide, antimony phosphide, phosphorus trichloride, trimethylphosphine, and triphenylphosphine. We address the actual drawback of the direct method or Rochow method using such phosphorus compounds as a co-catalyst, that is, the problem that the phosphorus compounds serve to increase the diorganodihalosilane content, but reduce the reaction rate and hence, the productivity of useful silane. We also intend to realize in a commercial plant an increase of production rate which has never been accomplished when the direct method is carried out using as an activator conventional additives known to improve activity or such compounds as monomethyldichlorosilane. In such efforts, we have found that the above objects are attained by adding a complex of the general formula (2) having a ligand in the form of an organophosphino compound of the general formula (3), typically an organic monophosphine compound of the general formula (3a) or an organic diphosphine compound of the general formula (3b), to be defined later, to the contact mass.

Quite unexpectedly, we have found that by adding a complex of the general formula (2) having a ligand in the form of an organophosphino compound of the general formula (3) to the reaction system, unlike the prior art means such as the introduction of metal atom clusters and the introduction of a gas phase low-molecular weight compound, only the production rate can be significantly increased while keeping the useful silane content substantially unchanged.

$L^1$ is an organophosphino compound of the following general formula (3):

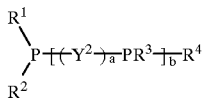

wherein $R^1$, $R^2$, $R^3$ and $R^4$ each are a monovalent hydrocarbon group, $Y^2$ is a divalent organic group, "a" is equal to 0 or 1, and "b" is an integer of 0 or greater, M is a metal atom forming a coordinate bond with $L^1$, $L^2$ is a hydrogen atom, halogen atom or π-accepting ligand directly attached to M, x is an integer of at least 1, y and z are integers satisfying $1 \leq y$, $0 \leq z$, and $1 \leq y+z \leq 6x$.

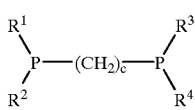

Herein $R^1$, $R^2$, $R^3$ and $R^4$ are as defined above, and "c" is an integer of 0 or greater.

The Grignard method had dominated in the industrial manufacture of organohalosilanes since its discovery by Kipping in 1904 until Rochow discovered the direct method. The Grignard method, however, is currently used only in the manufacture of special silanes and carbon functional silanes, because the Grignard method involves complex steps and has a potential danger due to a large amount of solvent. The later discovery of the direct synthesis method by Rochow (U.S. Pat. No. 2,380,995) was the innovation, following which the silicone industry took a remarkable leap. Because of high temperature reaction, however, the direct method made it difficult to explore a new sphere from the standpoint of organic synthesis. In this regard, paying attention to the history of organic synthesis until the discovery of the direct method, we have made efforts to find a way to new precision synthesis by incorporating tips of the indirect method or Grignard reaction into the direct method. On our belief, the essence in designing the catalyst function in the direct method resides in the number of coordinate bonding atoms acting on surface phases of the metal catalyst and silicon and the molecular modification of their conformation in atomic size. In order to bring up the catalyst design to reality, we borrowed the ground of conception from the cross-coupling reaction of the Grignard method (M. Kumada et al., J. Am. Chem. Soc., 106, 158 (1984)). The Grignard reaction is homogeneous reaction whereas the direct method is heterogeneous reaction. By substituting the metal in the cross-coupling reaction for the reaction surface solid phase in the direct method, we challenged to apply the feature of a complex catalyst, specifically a complex catalyst having a ligand in the form of an organophosphino compound, especially a complex catalyst having a ligand in the form of an organic monophosphine compound or organic diphosphine compound to the direct method of heterogeneous system.

In heterogeneous gas-solid reaction as in the direct method, prior art attempts to add metal powder and alloy powder to exert a new catalytic action fail because most of the charge becomes ineffective and the excess rather inhibits normal reaction. The prior art gas phase low-molecular weight compound is difficult to precisely control high-temperature reaction because it has a low evaporation temperature and lacks thermal stability.

The present invention using a complex catalyst, specifically a complex catalyst having a ligand in the form of an organophosphino compound as typified by an organic monophosphine compound or organic diphosphine compound in the direct method is a process using a coordination compound which is expected, by the probability theory, to interact with adjacent atoms on the reaction surface solid phase from a plurality of specific directions. Differently stated, it is a process of controlling the distance between coordinating atoms having catalysis. The process for preparing organohalosilanes using a complex catalyst differs utterly from the prior art improvements including the introduction of metal atom clusters and the introduction of a gas phase low-molecular weight compound. Based on this concept, we investigated a series of complex catalysts or organic phosphorus complexes. As a consequence, we have made a surprising discovery. The complex catalyst proposed herein is characterized by a higher evaporation temperature and a better thermal stability than the ligand alone because of the coordinate bond it forms, and by the formation of reactive sites on silicon surface in a pattern of sparsely distributed fine spots during reaction. Namely, the complex catalyst is effective for the production of organohalosilanes when used in very minute amounts as compared with the conventional activators, and especially effective for significantly improving the production rate without reducing the proportion of useful silane. This is what we have first and newly discovered.

We have also found that even on use of a silicon raw material of poor quality which is precluded of constant use in the prior art engineering formulation because of low reactivity, the addition of complex catalysts can impart a high activity surpassing the productivity associated with the use of metallic silicon of ordinary quality. It is believed that in order to optimize the total system for the manufacture of organohalosilanes involving the refining of silica stone into silicon, the addition of complex catalysts according to the present invention becomes a basis that allows for full use to advantage of an inexpensive silicon raw material of low purity grade.

Emphasizing again, the present invention is based on the discovery that the addition of complex catalysts of formula (2) to the reaction system can significantly increase the production rate without substantially changing the useful silane composition.

DESCRIPTION OF THE PREFERRED EMBODIMENT

The process for preparing oganohalosilanes according to the invention involves the steps of charging a reactor with a contact mass containing a metallic silicon powder and a copper catalyst, and introducing an organohalide-containing gas into the reactor to effect reaction to form organohalosilanes of the following general formula (1):

wherein R is a monovalent hydrocarbon group of 1 to 6 carbon atoms, X is a halogen atom, n and m each are an integer of 0 to 3, and the sum of n and m is 1 to 3. The process is characterized in that the contact mass further contains a complex of the general formula (2) having an organophosphino compound of the general formula (3) as a ligand.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 5 to 150 μm, corresponding to 50% of the mass base cumulative size distribution curve, in order that the metallic silicon powder have good fluidity.

The copper catalyst used herein may be selected from various forms of copper including elemental copper (or metallic copper) such as powdered copper and stamped copper, copper halides such as cuprous oxide, cupric oxide and copper chloride, and copper compounds such as copper acetate. Any of promoters such as zinc, tin, antimony and arsenic may be used as the co-catalyst. The co-catalyst may be used alone or in the form of an alloy with copper. Exemplary copper alloys are Cu—Zn, Cu—Sn, and Cu—Zn—Sn (or Sb or As). Examples of the co-catalyst which is used alone include zinc compounds such as metallic zinc, zinc chloride, zinc oxide, and zinc acetate, tin compounds such as metallic tin, tin chloride and tin oxide, antimony compounds such as metallic antimony, antimony chloride and antimony oxide, aluminum compounds such as metallic aluminum, aluminum chloride and aluminum oxide, metallic phosphorus, inorganic phosphorus compounds such as phosphorus trichloride and phosphorus oxide, and alkylphosphines such as trimethylphosphine and triphenylphosphine. The copper catalyst and co-catalyst may be separately admitted into the reactor.

An appropriate amount of the copper catalyst blended is about 0.1 to 10 parts, and more preferably about 2 to 8 parts by weight per 100 parts by weight of the metallic silicon powder. The amount of the co-catalyst blended is suitably determined among the commonly used amounts depending on its type and form. For example, zinc is used in an amount of 0.05 to 1 part by weight per 100 parts by weight of the metallic silicon powder. Tin, antimony and arsenic are used in a single or total amount of 0.001 to 0.05 part, especially 0.005 to 0.01 part by weight per 100 parts by weight of the metallic silicon powder.

The organohalide to be reacted with metallic silicon to form organohalosilanes of the formula (1) is selected depending on the type of the desired organohalosilane product, that is, the type of R in formula (1) wherein R is a monovalent hydrocarbon group of 1 to 6 carbon atoms, typically an alkyl, alkenyl or aryl group. Illustrative examples of the organohalide include methyl chloride, ethyl chloride, propyl chloride, methyl bromide, ethyl bromide, benzene chloride and benzene bromide. Of these, methyl chloride and benzene chloride are preferable. Methyl chloride is most useful in the industry because dimethyldichlorosilane produced therefrom finds a wide variety of applications as the raw material for many silicone resins. The organohalide is previously heated and gasified before it is admitted into the reactor. The organohalide gas may be fed alone or combined with an inert gas in a sufficient amount to fluidize the contact mass, the fluidizing amount being determined as appropriate from the diameter of the reactor and the superficial velocity.

According to the invention, a complex of the formula (2) is added to and blended with the contact mass containing the metallic silicon powder and the copper catalyst.

$L^1$ is an organophosphino compound of the following general formula (3):

wherein $R^1$, $R^2$, $R^3$ and $R^4$ each are a monovalent hydrocarbon group, $Y^2$ is a divalent organic group, "a" is equal to 0 or 1, and "b" is an integer of 0 or greater, M is a metal atom forming a coordinate bond with $L^1$, $L^2$ is a hydrogen atom, halogen atom or π-accepting ligand directly attached to M, x is an integer of at least 1, y and z are integers satisfying $1 \leq y$, $0 \leq z$, and $1 \leq y+z \leq 6x$.

The ligand $L^1$ is preferably an organic monophosphine compound of the following general formula (3a) or an organic diphosphine compound of the following general formula (3b).

Herein $R^1$, $R^2$, $R^3$ and $R^4$ are as defined above, and "c" is an integer of 0 or greater.

The monovalent hydrocarbon groups represented by $R^1$ to $R^4$ are preferably those of 1 to 12 carbon atoms, especially 1 to 8 carbon atoms. $R^1$, $R^2$, $R^3$ and $R^4$ may be the same or different. Illustrative examples include alkyl groups such as methyl, ethyl, propyl, isopropyl, butyl, isobutyl, tert-butyl, pentyl, cyclopentyl, hexyl, cyclohexyl, and octyl; alkenyl groups such as vinyl, allyl, propenyl, butenyl, and hexenyl; aryl groups such as phenyl, xylyl and tolyl; and aralkyl groups such as benzyl and phenylethyl. Of these, phenyl, methyl and ethyl are preferred, with phenyl being most preferred. $Y^2$ stands for a divalent organic group, that is, such a functional group that $Y^2H_2$ may become an alkane, alkene, cycloalkane, cycloalkene, metal compound thereof or aromatic compound thereof. The metal compound mentioned herein is a cycloalkene metal compound such as ferrocene. Preferably, $Y^2$ stands for alkylene, alkenylene and arylene groups having 1 to 20 carbon atoms, especially 1 to 10 carbon atoms. These groups may have some or all of the hydrogen atoms therein replaced by —COO groups or —CO—O—CO— groups (acid anhydride groups) or contain an ether oxygen atom or carbonyl group. The letter "a" is equal to 0 or 1, preferably 1, "b" is an integer inclusive of 0, preferably 0 to 5, and more preferably equal to 0, 1 or 2, and "c" is an integer inclusive of 0, and preferably 1 to 10.

Preferred examples of the organophosphino compound of the formula (3) which is the ligand $L^1$ in formula (2) include bis(diphenylphosphino)methane,
1,2-bis(diphenylphosphino)ethane,
1,3-bis(diphenylphosphino)propane,
1,4-bis(diphenylphosphino)butane,
1,5-bis(diphenylphosphino)pentane,
1,6-bis(diphenylphosphino)hexane,
1,7-bis(diphenylphosphino)heptane,
1,8-bis(diphenylphosphino)octane,
1,9-bis(diphenylphosphino)nonane,
1,10-bis(diphenylphosphino)decane,
triphenylphosphine,
2,2'-bis(diphenylphosphino)-1,1'-binaphthyl,
1,4-bis(diphenylphosphino)butane,
2,3-bis(diphenylphosphino)butane,
1,2-bis(diphenylphosphino)ethylene,
bis(diphenylphosphinoethyleneethyl)phenylphosphine,
1,1'-bis(diphenylphosphino)ferrocene,
1,6-bis(diphenylphosphino)hexane,
2,3-bis(diphenylphosphino)maleic anhydride,
1,2-bis(diphenylphosphino)propane,
bis(2-diphenylphosphinoethyl)phenylphosphine,
tris[2-(diphenylphosphino)ethyl]phosphine, and
1,2-bis(dimethylphosphino)ethane.

Preferred examples of the center metal M in formula (2) that forms a coordinate bond with the organophosphino compound or ligand $L^1$ include V, Cr, Mn, Fe, Co, Ni, Cu, Zn, Mo, Ru, Rh, Pd, Ag, Sn, Os, Ir, Pt, and Au. Of these metals, Mn, Fe, Co, Ni, Cu, Zn, Rh, Pd, Sn and Pt are especially preferred.

The other ligand $L^2$ in formula (2) is a hydrogen atom, halogen atom or π-accepting ligand such as carbonyl, cyclopentadienyl, benzene or olefin. Of these, halogen and hydrogen atoms are preferred.

The complexes may be used alone or in admixture of two or more although it is preferred to use a mixture of two or more complexes.

To improve the productivity of organohalosilane, an effective amount of the complex of formula (2) is used, the effective amount being determined on the basis of the entire amount of silicon and depending on the reaction time, scale and grade of metallic silicon. Preferably 1 to 50,000 parts, and especially 50 to 10,000 parts by weight of the complex is used per million parts by weight of silicon.

In the step of heating the contact mass or imparting catalytic activity to the contact mass, an inert gas is used for fluidizing the contact mass in the reactor. Such an inert gas may be nitrogen, helium or argon gas, for example, with the nitrogen gas being preferable from the economic standpoint. The flow velocity of the inert gas fed in this and subsequent steps is at least the minimum fluidization velocity of the contact mass, and preferably about 5 times the minimum fluidization velocity. A flow velocity below the range of the inert gas may often fail to achieve uniform fluidization of the contact mass. If the flow velocity of the inert gas is above the range, metallic silicon powder may be excessively scattered with increased losses of the inert gas and heat. It is recommended to recycle the inert gas and the organohalide.

After the contact mass is given catalytic activity as mentioned above, the organohalide is introduced into the reactor where gas-solid catalytic reaction takes place between the organohalide and metallic silicon to form organohalosilanes.

It is appreciated that the reaction is preferably effected at a temperature of 230 to 600° C., and especially 250 to 500° C. The reactor used herein may be a fluidized bed, stirred bed or fixed bed reactor though not limited thereto. From the industrial standpoint, a fluidized bed reactor capable of continuous operation is preferable.

EXAMPLE

Examples of the invention are given below by way of illustration and not by way of limitation. Parts are by weight.

Comparative Example 1

A fluidized bed reactor of carbon steel having a diameter of 75 mm and a height of 900 mm was charged with 100 parts of metallic silicon powder and 4 parts of a catalyst mixture based on metallic copper powder. Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated 6 times. Reported in Table 1 are the concentrations of impurities in the metallic silicon used, an average of silane production rate from the start to the end of reaction, and an average of cumulative composition of useful silane quantity.

Example 1

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro [bis(diphenylphosphino)methane]nickel(II) ($NiCl_2$(dppm)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 2

A fluidized bed reactor of carbon steel having a diameter of 75 mm and a height of 900 mm was charged with 100 parts of metallic silicon powder, 5 parts of a catalyst mixture based on copper oxide powder, and 0.15 part of dichloro [bis(diphenylphosphino)methane]nickel(II) ($NiCl_2$(dppm)). Then a gas mixture of methyl chloride and nitrogen was introduced into the reactor at a rate of 14.4 Nl/min and the reactor was heated at a temperature of 320° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 3

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro[1,2-bis(diphenylphosphino)ethane]nickel(II) ($NiCl_2$(dppe)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 4

A fluidized bed reactor of carbon steel having a diameter of 75 mm and a height of 900 mm was charged with 100 parts of metallic silicon powder, 5 parts of a catalyst mixture based on copper oxide powder, and 0.15 part of dichloro[1,2-bis(diphenylphosphino)ethane]nickel(II) ($NiCl_2$(dppe)). Then a gas mixture of methyl chloride and nitrogen was introduced into the reactor at a rate of 14.4 Nl/min and the reactor was heated at a temperature of 320° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 5

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro[1,3-bis(diphenylphosphino)propane]nickel(II) ($NiCl_2$(dppp)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 6

A fluidized bed reactor of carbon steel having a diameter of 75 mm and a height of 900 mm was charged with 100 parts of metallic silicon powder, 5 parts of a catalyst mixture based on copper oxide powder, and 0.15 part of dichloro[1,3-bis(diphenylphosphino)propane]nickel(II) ($NiCl_2$(dppp)). Then a gas mixture of methyl chloride and nitrogen was introduced into the reactor at a rate of 14.4 Nl/min and the reactor was heated at a temperature of 320° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 7

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro[1,4-bis(diphenylphosphino)butane]nickel(II) ($NiCl_2$(dppb)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 8

A fluidized bed reactor of carbon steel having a diameter of 75 mm and a height of 900 mm was charged with 100 parts of metallic silicon powder, 5 parts of a catalyst mixture based on copper oxide powder, and 0.15 part of dichloro[1,4-bis(diphenylphosphino)butane]nickel(II) ($NiCl_2$(dppb)). Then a gas mixture of methyl chloride and nitrogen was introduced into the reactor at a rate of 14.4 Nl/min and the reactor was heated at a temperature of 320° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 9

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro[2,5-bis(diphenylphosphino)pentane]nickel(II) ($NiCl_2$(dpppe)). Then methyl chloride was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 10

A fluidized bed reactor of carbon steel having a diameter of 75 mm and a height of 900 mm was charged with 100 parts of metallic silicon powder, 5 parts of a catalyst mixture based on copper oxide powder, and 0.15 part of dichloro[1,5-bis(diphenylphosphino)pentane]nickel(II) ($NiCl_2$(dpppe)). Then methyl chloride was introduced into the reactor at a rate of 14.4 Nl/min and the reactor was heated at a temperature of 320° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 11

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro [1,10-bis(diphenylphosphino)decane]nickel(II) (NiCl$_2$(dppd)). Then methyl chloride was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 12

A fluidized bed reactor of carbon steel having a diameter of 75 mm and a height of 900 mm was charged with 100 parts of metallic silicon powder, 5 parts of a catalyst mixture based on copper oxide powder, and 0.15 part of dichloro[1, 10-bis(diphenylphosphino)decane]nickel(II) (NiCl$_2$(dppd)). Then methyl chloride was introduced into the reactor at a rate of 14.4 Nl/min and the reactor was heated at a temperature of 320° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 13

A fluidized bed reactor of carbon steel having a diameter of 75 mm and a height of 900 mm was charged with 100 parts of metallic silicon powder, 4 parts of a catalyst mixture based on metallic copper powder, and 0.02 part of dichloro [bis(diphenylphosphino)methane]nickel(II) (NiCl$_2$(dppm)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 14

A fluidized bed reactor of carbon steel having a diameter of 75 mm and a height of 900 mm was charged with 100 parts of metallic silicon powder, 4 parts of a catalyst mixture based on metallic copper powder, and 0.02 part of dichloro [1,3-bis(diphenylphosphino)propane]nickel(II) (NiCl$_2$(dppp)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Example 15

A fluidized bed reactor of carbon steel having a diameter of 75 mm and a height of 900 mm was charged with 100 parts of metallic silicon powder, 4 parts of a catalyst mixture based on metallic copper powder, and 0.02 part of dichloro [1,10-bis(diphenylphosphino)decane]nickel(II) (NiCl$_2$(dppd)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 1 are the concentrations of impurities in the metallic silicon used, an average of silane production rate from the start to the end of reaction, and an average of cumulative composition of useful silane quantity.

Comparative Example 2

A fluidized bed reactor of carbon steel having a diameter of 75 mm and a height of 900 mm was charged with 100 parts of metallic silicon powder, 4 parts of a catalyst mixture based on metallic copper powder, and 0.2 part of copper phosphide. Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated 3 times. Reported in Table 1 are the concentrations of impurities in the metallic silicon used, an average of silane production rate from the start to the end of reaction, and an average of cumulative composition of useful silane quantity.

Comparative Example 3

A fluidized bed reactor of carbon steel having a diameter of 75 mm and a height of 900 mm was charged with 100 parts of metallic silicon powder and 4 parts of a catalyst mixture based on metallic copper powder. Then a gas mixture of methyl chloride and nitrogen was introduced into the reactor at a rate of 14.4 Nl/min. Separately, nitrogen gas was bubbled into a 0.1 mol/liter toluene solution of trichlorophosphine, obtaining trichlorophosphine vapor-carrying nitrogen gas, which was introduced into the reactor as well. The reactor was heated at a temperature of 310° C. Under the conditions, reaction was continued for 6 hours, following which the reaction was terminated. This experiment was repeated 3 times. Reported in Table 1 are the concentrations of impurities in the metallic silicon used, an average of silane production rate from the start to the end of reaction, and an average of cumulative composition of useful silane quantity.

Comparative Example 4

A fluidized bed reactor of carbon steel having a diameter of 75 mm and a height of 900 mm was charged with 100 parts of metallic silicon powder and 4 parts of a catalyst mixture based on metallic copper powder. Then a gas mixture of methyl chloride and nitrogen was introduced into the reactor at a rate of 14.4 Nl/min. Separately, nitrogen gas was bubbled into a 0.1 mol/liter toluene solution of trimethylphosphine, obtaining trimethylphosphine vapor-carrying nitrogen gas, which was introduced into the reactor as well. The reactor was heated at a temperature of 310° C. Under the conditions, reaction was continued for 6 hours, following which the reaction was terminated. This experiment was repeated 3 times. Reported in Table 1 are the concentrations of impurities in the metallic silicon used, an average of silane production rate from the start to the end of reaction, and an average of cumulative composition of useful silane quantity.

Comparative Example 5

A fluidized bed reactor of carbon steel having a diameter of 75 mm and a height of 900 mm was charged with 100 parts of metallic silicon powder and 4 parts of a catalyst mixture based on metallic copper powder. Then a gas mixture of methyl chloride and nitrogen was introduced into the reactor at a rate of 14.4 Nl/min. Separately, nitrogen gas was bubbled into a 0.1 mol/liter toluene solution of monomethyldichlorosilane (MH), obtaining monomethyldichlorosilane vapor-carrying nitrogen gas, which was introduced into the reactor as well. The reactor was heated at a temperature of 310° C. Under the conditions, reaction was continued for 6 hours, following which the reaction was terminated. This experiment was repeated 3 times. Reported in Table 1 are the concentrations of impurities in the metallic silicon used, an average of silane production rate from the start to the end of reaction, and an average of cumulative composition of useful silane quantity.

tetrachlorotetrakis[1,3-bis(diphenylphosphino)propane]tetracopper(II) ($Cu_4Cl_4(dppp)_4$). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 17

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro[1,3-bis(diphenylphosphino)propane]cobalt(I) ($CoCl_2(dppp)$). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 18

A fluidized bed reactor of carbon steel having a diameter of 75 mm and a height of 900 mm was charged with 100

TABLE 1

|     | Reaction temperature (° C.) | Fe [%] | Al [%] | Ca [%] | Additive | Additive concentration[a] (%/Si) | Production rate[b] (g/h) | Production rate standardization factor[c] | Useful silane content[d] (%) |
|---|---|---|---|---|---|---|---|---|---|
| CE1 | 310 | 0.26 | 0.13 | 0.07 | — | 0.00 | 258 | — | 87.2 |
| E1 | 310 | 0.29 | 0.14 | 0.06 | $NiCl_2(dppm)$ | 0.15 | 618 | 8.07 | 86.9 |
| E2 | 320 | 0.33 | 0.17 | 0.02 | $NiCl_2(dppm)$ | 0.15 | 536 | 6.22 | 86.7 |
| E3 | 310 | 0.29 | 0.14 | 0.06 | $NiCl_2(dppe)$ | 0.15 | 570 | 7.00 | 87.3 |
| E4 | 320 | 0.33 | 0.17 | 0.02 | $NiCl_2(dppe)$ | 0.15 | 395 | 3.07 | 86.3 |
| E5 | 310 | 0.29 | 0.14 | 0.06 | $NiCl_2(dppp)$ | 0.15 | 567 | 6.93 | 87.2 |
| E6 | 320 | 0.33 | 0.17 | 0.02 | $NiCl_2(dppp)$ | 0.15 | 520 | 5.87 | 86.6 |
| E7 | 310 | 0.29 | 0.14 | 0.06 | $NiCl_2(dppb)$ | 0.15 | 742 | 10.85 | 85.8 |
| E8 | 320 | 0.29 | 0.14 | 0.06 | $NiCl_2(dppb)$ | 0.15 | 508 | 5.60 | 86.8 |
| E9 | 310 | 0.33 | 0.17 | 0.02 | $NiCl_2(dpppe)$ | 0.15 | 634 | 8.42 | 88.2 |
| E10 | 320 | 0.29 | 0.14 | 0.06 | $NiCl_2(dpppe)$ | 0.15 | 497 | 5.35 | 86.7 |
| E11 | 310 | 0.33 | 0.17 | 0.02 | $NiCl_2(dppd)$ | 0.15 | 574 | 7.08 | 87.3 |
| E12 | 320 | 0.29 | 0.14 | 0.06 | $NiCl_2(dppd)$ | 0.15 | 420 | 3.64 | 87.5 |
| E13 | 310 | 0.33 | 0.17 | 0.02 | $NiCl_2(dppm)$ | 0.02 | 427 | 3.79 | 88.1 |
| E14 | 310 | 0.29 | 0.14 | 0.06 | $NiCl_2(dppp)$ | 0.02 | 546 | 6.45 | 87.7 |
| E15 | 310 | 0.29 | 0.14 | 0.06 | $NiCl_2(dppd)$ | 0.02 | 481 | 5.01 | 87.2 |
| CE2 | 310 | 0.26 | 0.13 | 0.07 | $Cu_3P$ | 0.20 | 276 | 0.41 | 89.8 |
| CE3 | 310 | 0.26 | 0.13 | 0.07 | $PCl_3$ | (e) | 161 | −2.16 | 88.0 |
| CE4 | 310 | 0.28 | 0.12 | 0.06 | $PMe_3$ | (e) | 138 | −2.68 | 89.6 |
| CE5 | 310 | 0.26 | 0.13 | 0.07 | MH | (e) | 288 | 0.68 | 88.1 |

Note:
[a]The concentration of the additive based on the weight of silicon
[b], [d]An average of six experiments for Comparative Example 1, an average of two experiments for Examples 1 to 15, and an average of three experiments for Comparative Examples 2 to 5
[c]Production rate standardization factor is a statistic calculated according to the following expression from an average (D) of production rate data in each Example, an average (m) of production rate data of six experiments in Comparative Example 1 and its standard deviation σ.
Standardization factor = (D − m)/σ
(e) 0.1 mol/liter toluene solution of each additive was introduced into the reactor by carrying it on nitrogen gas (together with methyl chloride).

Example 16

A fluidized bed reactor of carbon steel having a diameter of 75 mm and a height of 900 mm was charged with 100 parts of metallic silicon powder, 4 parts of a catalyst mixture based on metallic copper powder, and 0.15 part of parts of metallic silicon powder, 4 parts of a catalyst mixture based on metallic copper powder, and 0.15 part of dichlorobis[1,3-bis(diphenylphosphino)propane]iron(II) ($FeCl_2(dppp)_2$). Then a gas mixture of methyl chloride and nitrogen was introduced into the reactor at a rate of 14.4

Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 19

A fluidized bed reactor of carbon steel having a diameter of 75 mm and a height of 900 mm was charged with 100 parts of metallic silicon powder, 4 parts of a catalyst mixture based on metallic copper powder, and 0.15 part of chlorohydridebis[1,3-bis(diphenylphosphino)propane]iron (III) (FeHCl(dppp)$_2$). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 20

A fluidized bed reactor of carbon steel having a diameter of 75 mm and a height of 900 mm was charged with 100 parts of metallic silicon powder, 4 parts of a catalyst mixture based on metallic copper powder, and 0.15 part of chlorotris(triphenylphosphine)cobalt(I) (CoOCl(tpp)$_3$). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 21

A fluidized bed reactor of carbon steel having a diameter of 75 mm and a height of 900 mm was charged with 100 parts of metallic silicon powder, 4 parts of a catalyst mixture based on metallic copper powder, and 0.15 part of bis(triphenylphosphine)nickel(II) chloride (NiCl$_2$(tpp)$_2$). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 22

A fluidized bed reactor of carbon steel having a diameter of 75 mm and a height of 900 mm was charged with 100 parts of metallic silicon powder, 4 parts of a catalyst mixture based on metallic copper powder, and 0.15 part of chlorotris(triphenylphosphine)copper(I) (CuCl(tpp)$_3$). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 23

A fluidized bed reactor of carbon steel having a diameter of 75 mm and a height of 900 mm was charged with 100 parts of metallic silicon powder, 4 parts of a catalyst mixture based on metallic copper powder, and 0.15 part of chlorotris(triphenylphosphine)rhodium(I) (RhCl(tpp)$_3$). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 24

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro[1,1'-bis(diphenylphosphino)ferrocene]palladium(II) (PdCl$_2$(dppf)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 25

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro[1,2-bis(diphenylphosphino)ethane]palladium(II) (PdCl$_2$(dppe)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

Example 26

A fluidized bed reactor of carbon steel having a diameter of 75 mm and a height of 900 mm was charged with 100 parts of metallic silicon powder, 4 parts of a catalyst mixture based on metallic copper powder, and 0.15 part of dichloro[1,3-bis(diphenylphosphino)propane]palladium(II) (PdCl$_2$(dppp)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 2 are the concentrations of impurities in the metallic silicon used, an average of silane production rate from the start to the end of reaction, and an average of cumulative composition of useful silane quantity.

heated at a temperature of 310° C. Under the conditions, reaction was continued for 6 hours, following which the reaction was terminated. This experiment was repeated 3 times. Reported in Table 3 are an average of silane production rate from the start to the end of reaction, and an average of cumulative composition of useful silane quantity.

TABLE 2

|  | Reaction temperature (° C.) | Fe [%] | Al [%] | Ca [%] | Additive | Additive concentration[a] (%/Si) | Production rate[b] (g/h) | Production rate standardization factor[c] | Useful silane content[d] (%) |
|---|---|---|---|---|---|---|---|---|---|
| E16 | 310 | 0.29 | 0.14 | 0.06 | $Cu_4Cl_4(dppp)_4$ | 0.15 | 601 | — | 87.7 |
| E17 | 310 | 0.26 | 0.18 | 0.07 | $COCl_2(dppp)$ | 0.15 | 663 | 9.07 | 86.7 |
| E18 | 310 | 0.29 | 0.14 | 0.06 | $FeCl_2(dppp)_2$ | 0.15 | 652 | 8.83 | 86.2 |
| E19 | 310 | 0.26 | 0.18 | 0.07 | $FeHCl(dppp)_2$ | 0.15 | 554 | 6.65 | 86.0 |
| E20 | 310 | 0.26 | 0.18 | 0.07 | $CoCl(tpp)_3$ | 0.15 | 400 | 3.19 | 87.0 |
| E21 | 310 | 0.26 | 0.18 | 0.07 | $NiCl_2(tpp)_2$ | 0.15 | 505 | 5.55 | 87.3 |
| E22 | 310 | 0.26 | 0.18 | 0.07 | $CuCl(tpp)_3$ | 0.15 | 456 | 4.44 | 86.5 |
| E23 | 310 | 0.26 | 0.18 | 0.07 | $RhCl(tpp)_3$ | 0.15 | 411 | 3.44 | 87.5 |
| E24 | 310 | 0.29 | 0.14 | 0.06 | $PdCl_2(dppf)$ | 0.15 | 571 | 7.02 | 85.4 |
| E25 | 310 | 0.29 | 0.14 | 0.06 | $PdCl_2(dppe)$ | 0.15 | 639 | 8.55 | 86.7 |
| E26 | 310 | 0.29 | 0.14 | 0.06 | $PdCl_2(dppp)$ | 0.15 | 656 | 8.92 | 86.9 |

Note:
[a]The concentration of the additive based on the weight of silicon
[b], [d]An average of two experiments for Examples 16 to 26
[c]Production rate standardization factor is a statistic calculated according to the following expression from an average (D) of production rate data in each Example, an average (m) of production rate data of six experiments in Comparative Example 1 and its standard deviation σ.
Standardization factor = (D − m)/σ

As seen from Tables 1 and 2, whenever the complex catalyst is added, the production rate was increased without substantially reducing the useful silane content. This is better understood by comparing the standardization factor which is commonly employed as a statistic. Specifically, as compared with Comparative Examples having a standardization factor of production rate of less than 1σ or negative values, Examples of the invention have a standardization factor in excess of 3σ, which proves the noteworthy effect of the invention and the significance thereof.

Comparative Example 6

A fluidized bed reactor of carbon steel having a diameter of 75 mm and a height of 900 mm was charged with 100 parts of metallic silicon powder (containing 0.29% of Fe, 0.07% of Al and 0.06% of Ca) and 4 parts of a catalyst mixture based on metallic copper powder. Then a gas mixture of methyl chloride and nitrogen was introduced into the reactor at a rate of 14.4 Nl/min and the reactor was heated at a temperature of 310° C. Under the Example 27

A fluidized bed reactor of carbon steel having a diameter of 75 mm and a height of 900 mm was charged with 100 parts of metallic silicon powder (containing 0.29% of Fe, 0.07% of Al and 0.06% of Ca), 4 parts of a catalyst mixture based on metallic copper powder and 0.2 part of dichloro [1,3-bis(diphenylphosphino)propane]nickel(II) ($NiCl_2$ (dppp)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 3 are an average of silane production rate from the start to the end of reaction, and an average of cumulative composition of useful silane quantity.

TABLE 3

|  | Reaction temperature (° C.) | Fe [%] | Al [%] | Ca [%] | Additive | Additive concentration[a] (%/Si) | Production rate[b] (g/h) | Production rate standardization factor[c] | Useful silane content[d] (%) |
|---|---|---|---|---|---|---|---|---|---|
| CE6 | 310 | 0.29 | 0.07 | 0.06 | — | 0 | 90 | — | 87.8 |
| E27 | 310 | 0.29 | 0.07 | 0.06 | $NiCl_2(dppp)$ | 0.20 | 446 | 23.9 | 87.0 |

Note:
[a]The concentration of the additive based on the weight of silicon
[b], [d]An average of three experiments for Comparative Example 6 and an average of two experiments for Example 27
[c]Production rate standardization factor is a statistic calculated according to the following expression from an average (D) of production rate data in Example 27, an average (m) of production rate data of three experiments in Comparative Example 6 and its standard deviation σ.
Standardization factor = (D − m)/σ

Metallic silicon having an impurity composition as used in Comparative Example 6 has an extremely lower activity than the metallic silicon used in Comparative Example 1. Nevertheless, Example 27 within the scope of the invention is successful in acquiring a very high productivity even from such a silicon raw material which has extremely low activity under normal conditions. A comparison of their standardization factors reveals that the effect of inventive Example is by far superior.

Comparative Example 7

A fluidized bed reactor of carbon steel having a diameter of 75 mm and a height of 900 mm was charged with 100 parts of metallic silicon powder and 4 parts of a catalyst mixture based on metallic copper powder. Then a gas mixture of benzene chloride and nitrogen was introduced into the reactor at a rate of 14.4 Nl/min and the reactor was heated at a temperature of 510° C. Under the conditions, reaction was continued for 6 hours, following which the reaction was terminated. This experiment was repeated 3 times. Reported in Table 4 are the concentrations of impurities in the metallic silicon used, an average of silane production rate from the start to the end of reaction, and an average of cumulative composition of useful silane quantity.

Example 28

A fluidized bed reactor of carbon steel having a diameter of 75 mm and a height of 900 mm was charged with 100 parts of metallic silicon powder, 4 parts of a catalyst mixture based on metallic copper powder and 0.2 part of dichloro[1,3-bis(diphenylphosphino)propane]nickel(II) ($NiCl_2$(dppp)). Then a gas mixture of benzene chloride and nitrogen was introduced into the reactor at a rate of 14.4 Nl/min and the reactor was heated at a temperature of 510° C. Under the conditions, reaction was continued for 6 hours, following which the reaction was terminated. This experiment was repeated twice. Reported in Table 4 are the concentrations of impurities in the metallic silicon used, an average of silane production rate from the start to the end of reaction, and an average of cumulative composition of useful silane quantity.

As seen from Table 4, whenever the complex catalyst is added, the production rate of phenylchlorosilane as well was increased. This is better understood by comparing the standardization factor which is commonly employed as a statistic. Specifically, as compared with Comparative Example 7, Example 28 of the invention has a standardization factor in excess of $3\sigma$, which proves the noteworthy effect of the invention and the significance thereof.

Comparative Example 8

A fluidized bed reactor of carbon steel having a diameter of 75 mm and a height of 900 mm was charged with 100 parts of metallic silicon powder (containing 0.45% of Fe, 0.18% of Al and 7.3% of Ca) and 4 parts of a catalyst mixture based on metallic copper powder. Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated 3 times. Reported in Table 5 are an average of silane production rate from the start to the end of reaction, and an average of cumulative composition of useful silane quantity.

Example 29

A fluidized bed reactor of carbon steel having a diameter of 75 mm and a height of 900 mm was charged with 100 parts of metallic silicon powder (containing 0.45% of Fe, 0.18% of Al and 7.3% of Ca), 4 parts of a catalyst mixture based on metallic copper powder and 0.2 part of dichloro[1,3-bis(diphenylphosphino)propane]nickel(II) ($NiCl_2$(dppp)). Then a gas mixture of methyl chloride and nitrogen was introduced into the reactor at a rate of 14.4 Nl/min and the reactor was heated at a temperature of 310° C. Under the conditions, reaction was continued for 6 hours, following which the reaction was terminated. This experiment was repeated twice. Reported in Table 5 are an average of silane production rate from the start to the end of reaction, and an average of cumulative composition of useful silane quantity.

TABLE 4

| | Reaction temperature (° C.) | Fe [%] | Al [%] | Ca [%] | Additive | Additive concentration[a] (%/Si) | Production rate[b] (g/h) | Production rate standardization factor[c] | Useful silane content[d] (%) |
|---|---|---|---|---|---|---|---|---|---|
| CE7 | 510 | 0.26 | 0.13 | 0.07 | — | 0 | 381 | — | 63.5 |
| E28 | 510 | 0.26 | 0.13 | 0.07 | $NiCl_2$(dppp) | 0.20 | 619 | 3.3 | 64.1 |

Note:
[a]The concentration of the additive based on the weight of silicon
[b], [d]An average of three experiments for Comparative Example 7 and an average of two experiments for Example 28
[c]Production rate standardization factor is a statistic calculated according to the following expression from an average (D) of production rate data in Example 28, an average (m) of production rate data of three experiments in Comparative Example 7 and its standard deviation $\sigma$.
Standardization factor = $(D - m)/\sigma$

TABLE 5

| | Reaction temperature (° C.) | Fe [%] | Al [%] | Ca [%] | Additive | Additive concentration[a] (%/Si) | Production rate[b] (g/h) | Production rate standardization factor[c] | Useful silane content[d] (%) |
|---|---|---|---|---|---|---|---|---|---|
| CE8 | 310 | 0.45 | 0.18 | 7.3 | — | 0 | 132 | — | 85.6 |
| E29 | 310 | 0.45 | 0.18 | 7.3 | $NiCl_2$(dppp) | 0.20 | 422 | 13.0 | 85.1 |

TABLE 5-continued

| Reaction temperature (° C.) | Fe [%] | Al [%] | Ca [%] | Additive | Additive concentration[a] (%/Si) | Production rate[b] (g/h) | Production rate standardization factor[c] | Useful silane content[d] (%) |
| --- | --- | --- | --- | --- | --- | --- | --- | --- |

Note:
[a]The concentration of the additive based on the weight of silicon
[b], [d]An average of three experiments for Comparative Example 8 and an average of two experiments for Example 29
[c]Production rate standardization factor is a statistic calculated according to the following expression from an average (D) of production rate data in Example 29, an average (m) of production rate data of three experiments in Comparative Example 8 and its standard deviation σ.
Standardization factor = (D − m)/σ

Metallic silicon having an impurity composition as used in Comparative Example 8 has an extremely lower activity than the metallic silicon used in Comparative Example 1. Nevertheless, Example 29 within the scope of the invention is successful in acquiring a very high productivity even from such a silicon raw material which has extremely low activity under normal conditions. A comparison of their standardization factors reveals that the effect of inventive Example is by far superior.

By virtue of a complex catalyst, especially a metal complex of an organophosphino compound added to the contact mass, the invention is successful in producing organohalosilanes at a significantly improved production rate without reducing the selectivity of useful silane. Even when use is made of a silicon raw material which, when used in the standard formulation in the prior art, is less reactive and difficult to increase the activity to the level allowing for steady usage, the invention can impart thereto a high activity to surpass the productivity associated with the use of metallic silicon of ordinary quality. The invention permits the use of an inexpensive silicon raw material of low purity grade.

Japanese Patent Application No. 12-171419 is incorporated herein by reference.

Reasonable modifications and variations are possible from the foregoing disclosure without departing from either the spirit or scope of the present invention as defined by the claims.

What is claimed is:

1. A process for preparing oganohalosilanes comprising the steps of charging a reactor with a contact mass containing a metallic silicon powder and a copper catalyst, and introducing an organohalide-containing gas into the reactor to effect reaction to form organohalosilanes of the following general formula (1):

(1)

wherein R is a monovalent hydrocarbon group of 1 to 6 carbon atoms, X is a halogen atom, n and m each are an integer of 0 to 3, and the sum of n and m is 1 to 3, said contact mass further containing a complex of the following general formula (2):

(2)

wherein $L^1$ is an organophosphino compound of the following general formula (3):

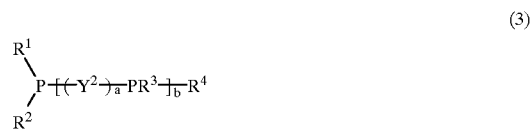
(3)

wherein $R^1$, $R^2$, $R^3$ and $R^4$ each are a monovalent hydrocarbon group, $Y^2$ is a divalent organic group, "a" is equal to 0 or 1, and "b" is an integer of at least 0,
M is a metal atom forming a coordinate bond with $L^1$,
$L^2$ is a hydrogen atom, halogen atom or π-accepting ligand directly attached to M,
x is an integer of at least 1, y and z are integers satisfying $1 \leq y$, $0 \leq z$, and $1 \leq y+z \leq 6x$.

2. The process of claim 1 wherein $L^1$ is an organic monophosphine compound of the following general formula (3a):

(3a)

wherein $R^1$, $R^2$ and $R^4$ are as defined above.

3. The process of claim 1 wherein $L^1$ is an organic diphosphine compound of the following general formula (3b):

(3b)

wherein $R^1$, $R^2$, $R^3$ and $R^4$ are as defined above, and "c" is an integer of at least 0.

4. The process of claim 1 wherein said contact mass contains at least two complexes of the general formula (2).

5. The process of claim 1 wherein the organohalide is methyl chloride or benzene chloride.

6. The process of claim 1 wherein reaction is effected at a temperature of 230 to 600° C.

7. The process of claim 1 wherein the reactor is a fluidized bed, stirred bed or fixed bed reactor.

* * * * *